US005773234A

United States Patent [19]

Pronovost et al.

[11] Patent Number: 5,773,234

[45] Date of Patent: Jun. 30, 1998

[54] METHOD AND DEVICE FOR CHLAMYDIA DETECTION

[75] Inventors: Allan D. Pronovost; Robert E. Klepper, both of San Diego; Catherine Pawlak, Encinitas, all of Calif.

[73] Assignee: Quidel Corporation, San Diego, Calif.

[21] Appl. No.: 511,337

[22] Filed: Aug. 7, 1995

[51] Int. Cl.$^{6}$ .................................................... G01N 33/53

[52] U.S. Cl. ......................... 435/7.36; 435/7.2; 435/7.32; 435/7.92; 435/7.94; 435/961; 435/975; 436/533; 436/536; 436/538; 436/544; 436/518; 436/808; 436/176; 436/177

[58] Field of Search .................................... 435/7.36, 7.2, 435/7.32, 7.34, 7.92, 7.94, 961, 967, 970, 975; 436/825, 533, 536, 538, 544, 518, 800, 175, 176, 177; 422/101

[56] References Cited

U.S. PATENT DOCUMENTS

| | | | |
|---|---|---|---|
| 4,652,518 | 3/1987 | Makela et al. . | |
| 4,663,291 | 5/1987 | Rose | 435/259 |
| 4,683,196 | 7/1987 | McLaughlin . | |
| 4,830,960 | 5/1989 | Appleton . | |
| 4,916,057 | 4/1990 | Thompson et al. . | |
| 5,047,325 | 9/1991 | Pronovost et al. | 435/7.36 |
| 5,047,326 | 9/1991 | Pronovost | 435/7.36 |
| 5,075,220 | 12/1991 | Pronovost | 435/7.36 |
| 5,075,221 | 12/1991 | Mauck et al. | 435/7.36 |
| 5,122,449 | 6/1992 | Gilbert et al. | 435/5 |
| 5,132,205 | 7/1992 | Pronovost et al. | 435/5 |
| 5,188,937 | 2/1993 | Schulte et al. | 435/7.36 |
| 5,387,511 | 2/1995 | Davidson et al. | 435/101 |
| 5,415,994 | 5/1995 | Imrich et al. | 435/5 |
| 5,484,706 | 1/1996 | Peterson et al. | 435/7.36 |
| 5,552,272 | 9/1996 | Bogart | 435/6 |

FOREIGN PATENT DOCUMENTS

| | | |
|---|---|---|
| 0 098 557 | 1/1984 | European Pat. Off. . |
| 0 253 912 | 1/1988 | European Pat. Off. . |
| 0 303 515 | 2/1989 | European Pat. Off. . |
| 0 325 045 | 7/1989 | European Pat. Off. . |
| 0 363 089 | 4/1990 | European Pat. Off. . |
| 0 363 090 | 4/1990 | European Pat. Off. . |
| 0 363 110 | 4/1990 | European Pat. Off. . |
| 0 363 989 | 4/1990 | European Pat. Off. . |
| 0 376 480 | 7/1990 | European Pat. Off. . |
| 0 444 303 | 9/1991 | European Pat. Off. . |
| 0 456 524 | 11/1991 | European Pat. Off. . |
| WO 86/02355 | 4/1986 | WIPO . |
| WO 88/08136 | 10/1988 | WIPO . |
| WO 89/08262 | 9/1989 | WIPO . |
| WO 90/13032 | 11/1990 | WIPO . |
| WO 94/15215 | 7/1994 | WIPO . |

OTHER PUBLICATIONS

Brade et al., "Chemical, Biological, and Immunochemical Properties of the Chlamydia psittaci Lipopolysaccharide," Infect. Immun. 54(2)568–74, Nov. 1986.

*Primary Examiner*—Carol A. Spiegel
*Attorney, Agent, or Firm*—Townsend and Townsend and Crew LLP

[57] ABSTRACT

A lateral flow assay device for detecting the presence of Chlamydia antigen in patient's samples comprises a flow matrix including a labelling zone and a capture zone. Labelling complex comprising antibodies specific for an epitope on the lipopolysaccharide antigen of Chlamydia is present within the labelling zone. Immobilized antibody specific for the same or another epitope of the lipopolysaccharide antigen of Chlamydia is located in the capture zone. The sample containing the Chlamydia antigen will flow first through the labelling zone, where it complexes with the labelling complex, and then to the capture zone, where it is captured by the immobilized antibody. Chlamydia antigen may be extracted from a patient sample, such as a endocervical swab, by first extracting the antigen in a strong base followed by neutralization with a zwitterionic detergent and a blocking protein present in a zwitterionic buffer.

14 Claims, 3 Drawing Sheets

METHOD AND DEVICE FOR CHLAMYDIA DETECTION

BACKGROUND OF THE INVENTION

The present invention relates generally to methods devices for detecting the presence of Chlamydia antigen in patient samples. More particularly, the present invention relates to a lateral flow assay system for the detection of Chlamydia antigen in liquid extracts from patient swab samples.

Chlamydia includes two species of intracellular parasites which infect man, other mammals, and birds. Chlamydia trachomatis is the species most commonly found in man and infects the urogenital organs, eyes, and respiratory track. Urogenital Chlamydia infection has become one of the most common sexually transmitted diseases and is a particular problem when passed on by mothers to newborn infants. Infants infected with Chlamydia often suffer from eye infection that can lead to blindness. Chlamydia infection in females which is left untreated can cause sterility.

The symptoms of Chlamydia infection are often vague and easily overlooked by doctors. Thus, there has been considerable interest in the development of assays for detecting Chlamydia infection, where the assays would be useful both to confirm suspected disease and to provide routine screening in particular patient populations, such as pregnant females.

Assays for the detection of Chlamydia infection present a number of challenges to the developer. In particular, Chlamydia is present at very low levels in samples from infected individuals (e.g., endocervical swab samples from infected females), requiring very high sensitivity. All tests for many microorganisms, such as Streptococcus and Candida, require a sensitivity of only about $5\times10^5$ organisms/ml. Chlamydia detection, in contrast, requires a sensitivity of from 10 to $10^2$ organisms/ml. While such sensitivities can be achieved with available technologies, such as ELISA, such tests generally require multiple steps and can be difficult to perform.

A second problem in the performance of Chlamydia assays relates to the nature of the patient sample. Detection of Chlamydia in the urogenital track of females requires a sample, typically using a endocervical swab. Such endocervical swab samples contain mucus, DNA, proteins, cellular debris, other bacteria, and polymorphonucleated leucocytes (PMNL's). The assays thus must provide for extraction and solubilization to separate the Chlamydia target antigen from infected cells contaminating materials. The extraction conditions, however, cannot be overly harsh since the antigen must remain in an immunologically recognizable form to permit detection in the immunoassay. In particular, the extraction conditions must avoid adhering or aggregating the target antigen with other solubilized materials in the complex mixtures created. Heretofore, extraction procedures utilized in Chlamydia tests have relied on complex procedures and formulations employing combinations of heat, surfactants, changes in pH, use of co-surfactants, cations, reducing agents, chelators, alkylating agents, and enzymatic digestion. In addition to being complex, the procedures have often been only minimally effective and often times require reagents which are not readily stored and useful in immunoassay kits. A particular extraction method employing strong alkali followed by acid neutralization is described in WO 89/08262. Such extraction method, however, led to assays with only moderate sensitivity.

Chlamydia tests based on a membrane assay format have been commercially developed. One such system is the SureCell™ assay available from Eastman Kodak, Rochester, N.Y. That assay uses a positively charged support to capture negatively charged Chlamydia antigen. Once captured on the membrane, the Chlamydia antigen is detected with a labeled antibody specific for the lipopolysaccharide of Chlamydia. These assays have moderate sensitivity and are prone to interference from the sample.

For these reasons, it would be desirable to provide assays and devices for the detection of Chlamydia in patient samples. The assays should be sensitive and specific for Chlamydia (i.e., being non-cross-reactive with organisms other than Chlamydia), and should require as few steps as possible for their performance. The assays should further provide rapid results, and should be suitable for use with a variety of samples suspected of containing Chlamydia, particularly swab samples for detecting Chlamydia in the urogenital track. The assays should still further be suitable for use in a variety of different environments, including in clinical and other laboratories, at the point of care, and by patients themselves (self-testing).

SUMMARY OF THE INVENTION

The present invention provides assays, devices, and kits for the detection of Chlamydia in patient samples, particularly in endocervical swab samples. The assays rely on applying a specimen containing solubilized Chlamydia antigen obtained from the sample onto a matrix defining a flow path including at least a labelling zone and a capture zone. The labelling zone contains non-bound labelling complex comprising a visible label bound to a capture binding substance specific for chlamydial lipopolysaccharide, particularly an epitope of the KDO moiety of the Chlamydia lipopolysaccharide antigen. The capture zone contains an immobilized labelling binding substance which is also specific for chlamydial lipopolysaccharide, such as an epitope of the KDO moiety of Chlamydia lipopolysaccharide antigen. The solubilized sample will thus flow through the labelling zone where the Chlamydia antigen, if present, will bind to the labelling complex. The labelling complex-bound antigen will continue to flow into the capture zone where it will be captured by the immobilized labelling binding substance, and will accumulate until sufficient label has been collected to be visible to the user. The appearance of visible label within the labelling zone is thus diagnostic of Chlamydia initially present in the sample.

The capture binding substance and the labelling binding substance are each specific for the same epitope on the KDO moiety of Chlamydia lipopolysaccharide or for different epitopes on the KDO moiety of Chlamydia lipopolysaccharide antigen. In one aspect of the invention, the capture binding substance and the labelling binding substance are antibodies. Labelling complex comprising antibodies specific for an epitope on the lipopolysaccharide antigen of Chlamydia is present within the labelling zone. Immobilized antibody specific for the same or another epitope of the lipopolysaccharide antigen of Chlamydia is located in the capture zone.

In a preferred aspect of the assay of the present invention, the solubilized antigen is obtained by pretreating a endocervical swab sample to extract the Chlamydia antigen and to neutralize the extract prior to applying the specimen to the matrix. It has been found that initial extraction of the antigen by incubation of the swab sample with a strong base, such as sodium hydroxide (NaOH), releases the lipopolysaccharide antigen from the complex. Subsequent neutralization with a zwitterionic detergent and a blocking protein, such as an albumin, particularly bovine serum albumin (BSA), further promotes solubilization of the antigen and inhibits aggregation of the antigen and interference from other substances present in the solubilized mixture.

Devices according to the present invention comprise a matrix defining a flow path including at least a labelling zone and a capture zone. Labelling complex is present within the labelling zone, and comprises a visible label bound to a binding substance specific for chlamydial lipopolysaccharide, particularly an epitope of the KDO moiety of Chlamydia lipopolysaccharide antigen. Binding substance specific for chlamydial lipopolysaccharide, particularly an epitope of the KDO moiety of Chlamydia lipopolysaccharide antigen is also immobilized within the capture zone so that it will remain fixed under the conditions of the assay so that it can capture and immobilize the antigen-bound labelling complex. The labelling complex initially present in the labelling zone, of course, will not be immobilized, and instead will be introduced in a manner so that it is fully mobilized by the passage of the solubilized sample and thus free to react with labelling complex and travel with said labelling complex to the capture zone.

Kits according to the present invention will include the assay device, generally as described above, in combination with a swab receptacle, a first reagent container holding a basic solution for initially incubating the swab in the receptacle, and a second reagent container holding a solution of a zwitterionic detergent and a blocking protein for neutralizing a sample which has been extracted using the basic solution. The device, swab receptacle, and both reagent containers will further be present in packaging, such as a box, bag, heat shrink display card, or the like, for completing the kit. Optionally, the kit may further comprise written instructions for setting forth the steps necessary to perform the assay of the present invention.

The assays, devices, and kits of the present invention have been found to provide assays with very high sensitivities and specificities. In particular, the data in the Experimental section of the present invention will demonstrate that the assays of the present invention have a sensitivity of 90% for symptomatic patients and 94% for asymptomatic patients. The specificity, i.e., the ability to distinguish from other microorganisms, is above 99%. The ability to achieve such high sensitivities and specificities using a lateral flow assay detection protocol could not have been predicted prior to the work reported in the present application.

DESCRIPTION OF THE SPECIFIC EMBODIMENTS

Figure 1:
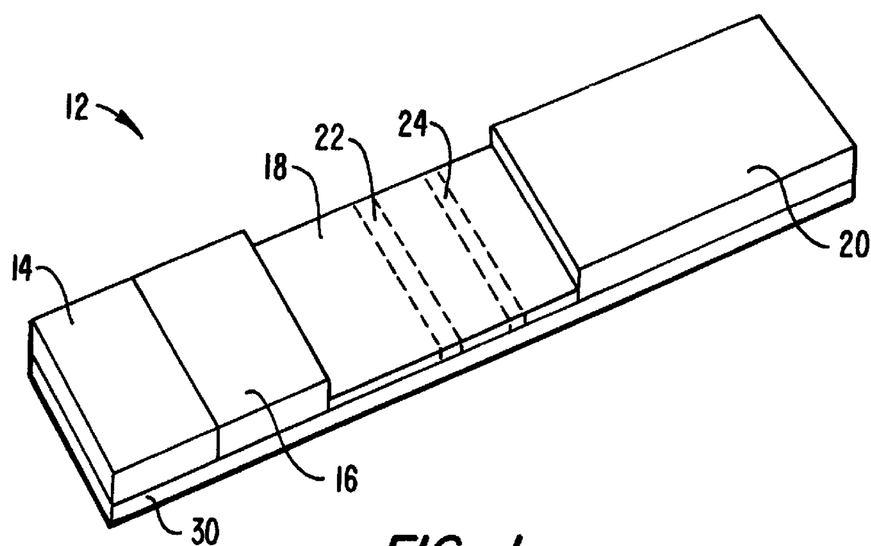
FIG. 1 illustrates an assay matrix including a sample receiving zone, a labelling zone, a capture zone, and an absorbent pad, constructed for detecting Chlamydia antigen in accordance with the principles of the present invention.

According to the present invention, assays, devices, and kits are provided for protecting the presence of Chlamydia in patient samples. The detection is immunological and relies on antibodies specific for chlamydial lipopolysaccharide (LPS), in particular for an epitope on the KDO moiety of Chlamydia lipopolysaccharide antigen. As this antigen is both Chlamydia-specific (free from cross-reactivity with other bacteria) and is conserved among all species of Chlamydia, the tests of the present invention will be useful for detecting both Chlamydia trachomatis and Chlamydia psitaccai, which are both potentially found in humans. The assays and devices of the present invention are particularly intended for the detection of Chlamydia trachomatis which may be present in vaginal secretions from infected female patients. In such cases, the samples will be obtained using conventional techniques which employ swabs for obtaining cellular specimens from the patient's cervix. Such endocervical swab samples will preferably be treated according to the preferred extraction protocol described below. The assays of the present invention, however, are also useful for detecting Chlamydia in other samples in which it may be present, including sputum, nasal secretions, pharyngeal exudates, and the like, where respiratory infection may be detected.

The preferred method of the present invention for extracting Chlamydia antigen from endocervical swab samples comprises an extraction step followed by a neutralization step. The swab is initially extracted in a strong base, typically 0.05 N to 0.3 N sodium hydroxide (NaOH), at room temperature for a time sufficient to release the antigen, typically from 0.1 min to 10 min. The extraction is preferably performed in the presence of 0.05 to 0.3 M NaCl. After extraction, the extract is neutralized by adding a zwitterionic detergent, such as 3-[(3-cholamidopropyl)-dimethylammonio]-1-propanesulfonate (CHAPS), and a blocking protein, such as an albumin, particularly bovine serum albumin (BSA), present in a zwitterionic buffer to the extract. It has been found that the combination of zwitterionic detergent and blocking protein in the zwitterionic buffer provides and maintains adequate solubilization of the antigen so that it is readily detected in the lateral flow protocols described hereinafter.

By including the zwitterionic detergent and the blocking protein in the extraction step, sensitivities 10 to 50-fold higher than those achieved by the prior alkali extraction method of WO 89/08262 have been obtained. Moreover, provision of a zwitterionic buffer in the neutralization medium provides a 5 to 10-fold increase in sensitivity over cationic buffers. Suitable zwitterionic buffers include TRICINE®; (N-[2hydroxy-1, 1bis(hydroxymethyl)ethyl] glycine; TAPSO (3-[Ntris(hydroxymethyl)methylamino]-2-hydroxypropanesulfonic acid); and BES (2-[bis(2-hydroxyethyl)amino]ethanesulfonic acid). Preferably, the zwitterionic buffer is incorporated as a diluent buffer in the sample and label zones of the device of the present invention and as a blocking solution buffer in the capture zone.

The presence of NaCl in the extraction buffer is beneficial since it helps prevent false positives associated with mild extraction conditions. While false positives are not a problem with harsh extraction conditions, e.g. 80° C. to 100° C. for several minutes, such conditions are inconvenient and unsafe.

The devices of the present invention will be suitable for providing "one-step" or "lateral flow" detection of the Chlamydia antigen in the solubilized extract. In particular, after the antigen has been extracted, it will be necessary only to apply a predetermined volume of the extract to the assay device, wait for a predetermined time, and thereafter read the assay results without performing any additional steps. Such lateral flow assay devices and methods are well described in the patent and technical literature.

See, for example, U.S. Pat. Nos. 5,415,994; 4,943,522; 4,861,711; 4,857,453; 4,855,240; 4,775,636; 4,730,017; 4,361,537; 4,235,601; 4,168,146; 4,094,647; European Patent Application Nos. 451 800; 158 746; 276 152; 306 772; British Patent Application No. 2,204,398; and PCT Publication WO 94/15215, each of which is incorporated herein by reference.

The devices of the present invention generally comprise a matrix composed of material which allows for capillary flow of the extracted sample solution along the flow path. The matrix will define at least a labelling zone having a means for specifically labelling Chlamydia antigen present in the sample and a capture zone having means for capturing the labeled antigen. Usually, the matrix will further define a sample receiving zone upstream of the labelling zone and an absorptive matrix downstream of the capture zone. By "upstream from the labelling zone" it is meant that sample applied to the sample receiving zone will flow into the labelling zone. Similarly, By "downstream from the capture zone" it is meant that sample will flow into the absorptive path in order to maintain the desired capillary flow along the flow bath.

The matrix of the assay device will typically be capable of non-bibulous lateral flow. By "non-bibulous lateral flow", it is meant liquid flow in which all of the dissolved or dispersed components of the liquid are carried at substantially equal rates and with relatively unimpaired flow laterally through the membrane, as opposed to preferential retention of one or more components as would occur, e.g., in materials capable of adsorbing or imbibing one or more components.

A typical non-bibulous matrix material is a high density polyethylene sheet material, such as the type manufactured by Porex Technologies Corp. of Fairburn, Ga. USA. This membrane has an open pore structure with a typical density, at 40% void volume, of 0.57 gm/cc and an average pore diameter of 1 to 250 micrometers, generally from 3 to 100 micrometers. The optimum pore diameter for the membrane for use in the invention is about 90 to about 140 $\mu$m. The membranes are from a few mils (0.001 in) to several mils in thickness, typically in the range of from 5 or 10 mils and up to 200 mils. The membrane is generally backed by a generally water impervious layer, but may be totally free standing. Other non-bibulous membranes, such as polyvinyl chloride, polyvinyl acetate, copolymers of vinyl acetate and vinyl chloride, polyamide, polycarbonate, nylon, glass fiber, orlon, polyester, polystyrene, and the like, or blends can also be used.

Bibulous materials, such as untreated paper, nitrocellulose, derivatized nylon, cellulose and the like may also be used following processing to provide non-bibulous flow. Blocking agents may block the forces which account for the bibulous nature of bibulous membranes. Suitable blocking agents include whole or derivatized bovine serum albumin or albumin from other animals, whole animal serum, casein, and non-fat dry milk.

The matrix comprises at least two zones, a sample receiving zone and a capture zone. The size and shape of the matrix are not critical and may vary. The matrix defines a lateral flow path. Generally, the matrix is rectangular and flow path is axial.

Solubilized patient sample, typically an extracted endocervical swab specimen as described above, is applied to the matrix at the sample receiving zone. The sample receiving zone may contain a neutralizing agent which will neutralize the extraction solution prior to the assay. Usually, however, neutralization will have been achieved in the neutralization step of the extraction procedure described above.

Generally, the labelling zone is present on the matrix flow path between the sample receiving zone and the capture zone. The labelling zone contains a means for specifically labelling the target analyte. The labelling means will generally be a labeled immunoglobulin, such as an antibody, specific for the target analyte, i.e., an epitope on the KDO moiety of the Chlamydia LPS antigen. The immunoglobulins may be antibodies of any isotype, such as IgE, IgG, or IgM, Fab fragments, $F(ab')_2$ fragments, Fab' fragments, or the like. Alternatively, the labelling means may be a non-immunoglobulin labelled compound which specifically binds the target analyte. For example, if the target analyte is a receptor molecule, the labelling means may be a labeled ligand for that receptor molecule. Hereinafter, the term "binding substance" will be understood to refer to immunoglobulins and as well as other substances which specifically bind target analytes.

Antibodies specific for chlamydial LPS, particularly for the KDO moiety of Chlamydia (LPS) may be obtained by conventional antibody development techniques. See e.g., Harlow and Lane, eds., *Antibodies; A Laboratory Manual, and Laboratories*, Coldspring Harbor Laboratory, Coldspring, N.Y. Suitable immunogens for preparing the antibodies include the elementary bodies of a wide variety of Chlamydia trachomatis and Chlamydia psitaccai serovars. Suitable antibodies will have a binding affinity to the KDO moiety of at least about $10^7 M^{-1}$, preferably at least $10^5 M^{-1}$. Suitable monoclonal antibodies which may be used for performing the assays of the present invention are commercially available from Oy Medix Biochemica AB, Kauniainen, Finland. In particular, antibodies suitable as the labelling antibody in the methods of the present invention may be obtained from the clone designated 6701, while the capture antibody may be obtained from the clone designated 6703.

The labels may be soluble or particulate and may include dyed immunoglobulin binding substances, simple dyes or dye polymers, dyed latex beads, dye-containing liposomes (such as described in U.S. Pat. No. 4,695,554, incorporated herein by reference), dyed cells or organisms, or metallic, organic, inorganic, or dye sols. The labels may be bond to the analyte-specific immunoglobulins by a variety of means which are well known in the art such as described in U.S. Pat. Nos. 4,863,875 and 4,373,932, each of which is incorporated herein by reference.

As the treated sample flows through the labelling zone, the target analyte in the sample binds the labelled antibody thereby indirectly labelling the target analyte. The sample continues to flow into the capture zone on the matrix.

A compound capable of specifically binding the labelled target analyte is immobilized in the capture zone. Generally, target analyte-specific immunoglobulins will be immobilized in the capture zone. As the sample flows into the capture zone labelled target analytes will bind the immobilized immunoglobulins thereby retaining label in the capture zone.

The presence of analyte in the sample may then be determined by visual identification of label retention in the capture zone.

The capture zone of devices of the present invention may include a procedure control region or line. The procedure control line is generally located downstream of the analyte specific binding compound immobilized in the capture zone. Retention of label by the procedural control line indicates that the sample has flowed through the capture zone and contacted the immobilized target specific binding substance. Specific methods for incorporating a control region are described in detail in the Experimental section.

The accumulation of visible label may be assessed either visually or by optical detection devices, such as reflectance analyzers, video image analyzers and the like. The accumulation of visible label can be assessed either to determine the presence or absence of label in the capture zone or the visible intensity of accumulated label which may then be correlated with the concentration or titer (dilution) of analyte in the patient sample. The correlation between the visible intensity of accumulated label and analyte concentration may be made by comparison of the visible intensity to a reference standard. Optical detection devices may be programmed to automatically perform this comparison by means similar to that used by the Quidel Reflective Analyzer, Catalog No. QUO801 (Quidel Corp., San Diego, Calif.). Visual comparison is also possible by visual evaluation of the intensity and a color key such as used in the Quidel Total IgE Test Catalog No. 0701 (a multi-step ELISA assay). Thus, target analyte levels may be determined by devices of the present invention.

The devices of the present invention may further include an end-of-assay indicator to signal the test read time to the operator. The end-of-assay indicator is generally located on the matrix downstream from the capture zone.

A bibulous absorbent zone is generally included in the devices of the present invention. The absorbent zone is located downstream from the capture zone. The absorbent zone is a means for removing excess sample and unbound label from the matrix of the device. Generally, the absorbent zone will consist of an absorbent material such as filter paper, a glass fiber filter, or the like.

The present invention further provides kits for the pretreatment of endocervical swab samples and detection of Chlamydia antigen in those samples using the devices and methods of the present invention. The kits generally comprise the device as described above, a first container including the extraction solution, a second reagent container containing the neutralization solution, and a swab receptacle for washing the swab in the first and second reagents. The device, reagent containers, and swab receptacle will generally be included together and packaging of the type conventional for immunoassay kits, e.g., boxes, bags, cylinders, shrink wrap cards, and the like. Optionally, the kit may further include written instructions setting forth the method steps of the present invention.

Figure 2:
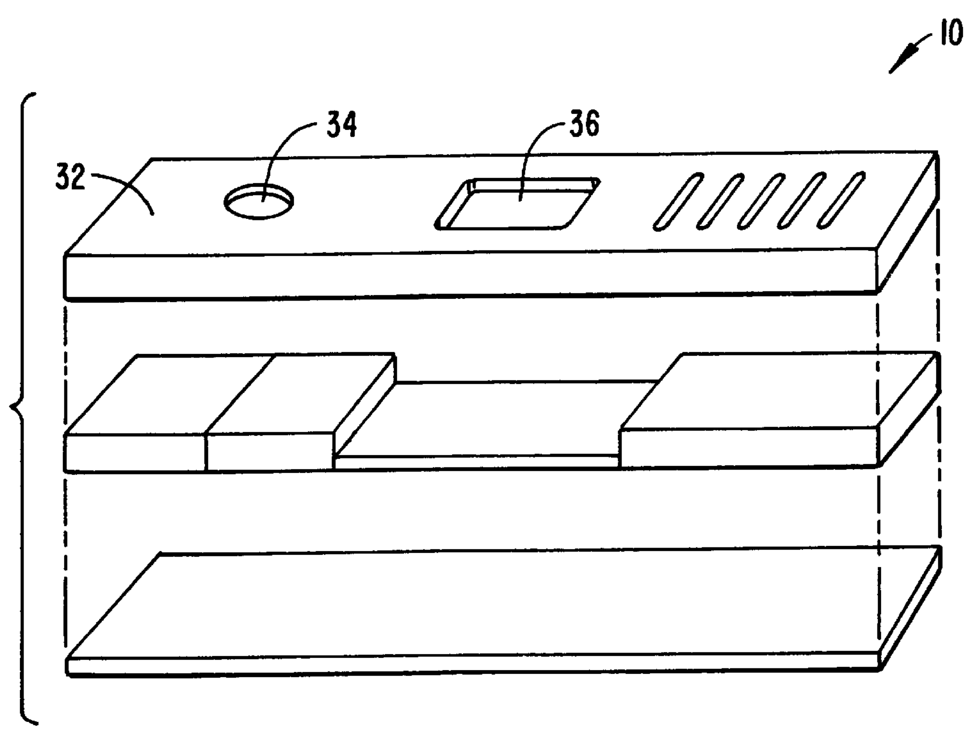
FIG. 2 illustrates an assembly technique for incorporating the assay matrix of FIG. 1 into a device having a suitable housing or cover.

Referring now to FIGS. 1 and 2, a device 10 useful for performing the assay methods of the present invention will be described. The device 10 includes an assay matrix 12 including a sample receiving pad 14, a labelling pad 16, and a capture pad 18. An absorbent pad 20 is also provided in order to absorb all liquid sample applied to the sample receiving zone 14 so that said sample will flow completely through the matrix. Labelling complex comprising the anti-Chlamydia antibody bound to a visible label will be present (but unbound) within the labelling pad 16, while immobilized antibody for capturing the Chlamydia antigen will be bound within a capture region 22 within the capture pad 18. Usually, a control region 24 will also be provided, as generally discussed above. The assay matrix 12 will include a backing 30, and the device 10 will be completed by attachment of cover 32 over the matrix 12 and backing 30, as best illustrated in FIG. 2. The cover 32 includes a sample application port 34 at a capture pad viewing port 36.

Figure 3:
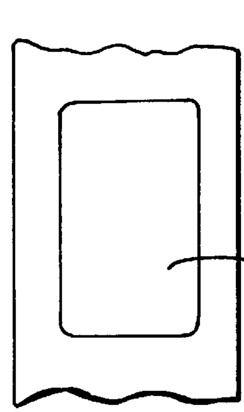
FIG. 3 is a detailed view of the device of FIG. 2, shown prior to performance of an assay, i.e., without visible label in the capture zone thereof.
Figure 4:
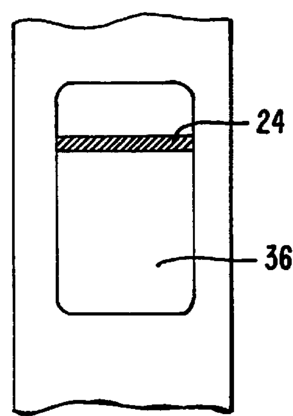
FIG. 4 is a view similar to FIG. 2, shown with label present in the control region of the capture zone.
Figure 5:
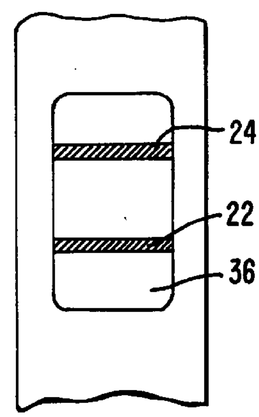
FIG. 5 is a view similar to FIGS. 3 and 4, shown with label present within both the control and assay regions of the capture zone.

The results of the assay are read through the capture zone aperture 36, as best illustrated in FIGS. 3–5. Initially, prior to application of sample, the capture pad 18 through aperture 36 will appear clean, i.e., free from captured label, as illustrated in FIG. 3. After application of a negative sample, i.e., one which does not contain Chlamydia antigen, the capture pad 18 will appear as illustrated in FIG. 4, i.e., with appearance of label along the control region 24, but no label within the test region 22. When the sample is positive, in contrast, the capture pad 18 will appear as illustrated in FIG. 5, i.e., with label accumulated in both the control region 24 and the test region 22.

The following examples are offered by way of illustration, not by way of limitation.

EXPERIMENTAL

Example 1

Preparation of a Lateral Flow Assay Device for Detecting Chlamydia

Lateral flow nonbibulous assay test strips were constructed to include three active zones and a fourth absorbent zone which acts as a wick or sink to receive sample flow from the active zones. The active zones comprise a sample receiving zone, a labelling zone, and a capture zone, as described generally above and in detail below.

Preparation of the Sample Receiving Zone

The sample receiving zone was prepared from Sontara® 0-100 DuPont Orlon® spunlace fabric. The fabric was rendered nonbibulous by saturating with methylated bovine serum albumin (methylated BSA). The conversion to nonbibulous material was achieved by treatment at 39 $\mu l/cm^2$ with a 10 mg/ml solution of the methylated BSA in 100 mM TRICINE buffer, pH 8.0 at room temperature for 5–30 minutes. The pad of Sontara® was then frozen at −70° C. along with a lyophilization flask for at least an hour. The Sontara® membrane was then lyophilized overnight on a Virtis Freezemobile. The treated sample receiving zone was cut into 11×9 mm rectangles with the spunlace fibers being parallel to the longer side of the pad.

Antibodies

Capture antibody was mouse monoclonal antibody to Chlamydia, clone designated 6703, purchased from Oy Medix Biochemica, Finland. Splenocytes of immune mouse (immunized with elementary bodies of *C. trachomatis* Serovar LGV2) were fused with myeloma cell line and grown in vitro in a hollow-fiber cell culture. The immunoglobulin was isolated from culture supernatant by FPLC Protein A affinity purification using citrate buffer, pH 4.5, elution. Eluent was dialyzed to 0.9% NaCl with 0.1% $NaN_3$ as a preservative and supplied in this form at the concentration of 1 mg/ml. The clone 6703 is genus specific, anti-Chlamydia LPS antibody and belongs to $IgG_{2a}$ class. Its chemical identity was assessed by isoelectric focusing with internal calibrators and a previous reference lot. Immunoreactivity was determined by antigen coated ELISA titration against the previous reference lot.

Label antibody was mouse monoclonal antibody to Chlamydia, clone designated 6701, purchased from Oy Medix Biochemica, Finland. Splenocytes of immune mouse (immunized with elementary bodies of *C. trachomatis* Serovar LGV2) were fused with myeloma cell line and grown in vitro in a hollow-fiber cell culture. The immunoglobulin was isolated from culture supernatant by FPLC Protein A affinity purification using citrate buffer pH 4.5, elution. Eluent was dialyzed to 0.9% NaCl with 0.1% $NaN_3$ as a preservative and supplied in this form at the concentration of 1mg/ml. The clone 6701 is genus specific, anti-Chlamydia LPS antibody and belongs to $IgG_1$ class. Its chemical identify was assessed by isoelectric focusing with internal calibrators and a previous reference lot. Immunoreactivity was determined by antigen coated ELISA titration against the previous reference lot.

Preparation of Labelling Zone

Light-blue "Control" beads (Polymer Labs) were diluted to 1.25% solids with 25 Mm tris-HCl buffer, pH 8.0 containing glucose oxidase at 0.5 mg/ml, final concentration, and rotated overnight at room temperature. The bead preparation was then centrifuged for three minutes, and the supernatant removed by aspiration. The bead pellet was then resuspended in 0.5 ml of the 10 mg/ml methylated BSA in 50 Mm tris-HCl buffer, pH 8.0. This mixture was rotated end-over-end for four hours at room temperature, and the bead preparation centrifuged to recover the pellet. The supernatant was aspirated, and the pellet was suspended in 10 mg/ml methylated BSA at 1% solids.

Dark-blue "Test" beads for labelling analyte, containing monoclonal anti-Chlamydia label antibody, were prepared in a similar manner. Dark-blue carboxylated beads (Bangs Laboratory) were diluted to 1.25% solids with 25 Mm tris-HCl buffer, pH 8.0 containing anti-Chlamydia monoclonal antibody at 0.5 mg/ml, final concentration, and rotated overnight at room temperature. The bead preparation was then centrifuged for three minutes, and the supernatant removed by aspiration. The bead pellet was then resuspended in 0.5 ml of 10 mg/ml methylated BSA in 50 Mm tris-HCl buffer, pH 8.0. This mixture was rotated end-over-end for four hours at room temperature, and the bead preparation centrifuged to recover the pellet. The supernatant was aspirated and the pellet was suspended in 10 mg/ml methylated BSA at 1% solids.

Finally, to prepare the labelling zone containing both test and control beads, the test and control beads were diluted with methylated BSA in 100 mM TRICINE buffer, pH 8.0, to a concentration of 0.04%. The resultant mixture was poured onto a Sontara 0-100 DuPont spunlace fabric at 39 $\mu l/cm^2$ and lyophilized as described above for the sample zone.

Preparation of Capture Zone Membrane

Sartorius nitrocellulose having a pore size of 8 $\mu$m was affixed to an X-Y chart recorder, and Chlamydia capture bands were formed as 2-cm spaced parallel lines by dispensing 1 mg/ml monoclonal anti-Chlamydia capture antibody using a plotter pen operated in the manual mode. These lines were active with Chlamydia contained in a sample. The membrane was then spotted in parallel lines 0.3 cm above previously-spotted anti-Chlamydia capture line with a 2 mg/ml rabbit anti-glucose oxidase in PBS buffer. These are lines reactive with the glucose oxidase on the control beads. After air drying for 10 min at room temperature, the nitrocellulose membrane was blocked by soaking in 10 mg/ml methylated BSA in the 100 mM TRICINE buffer, pH 8, for 15 min at room temperature. The blocked membrane was then blotted, allowed to air dry and stored in a desiccator at room temperature until assembly of the device.

Assembly of the Device

Figure 6A:
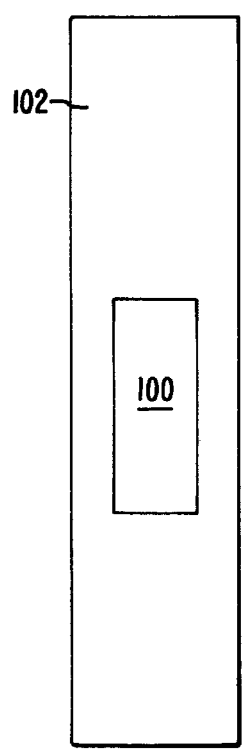
FIG. 6A–6D illustrate the construction of the test device utilized in the Experimental section.
Figure 6B:
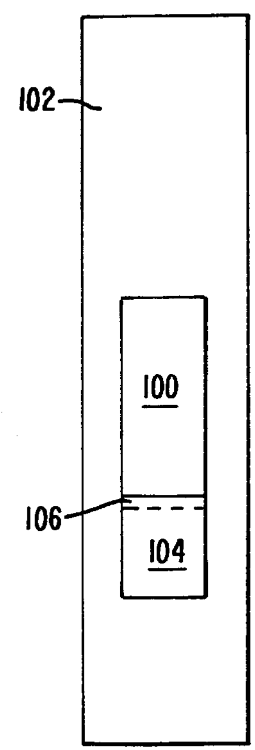
Figure 6C:
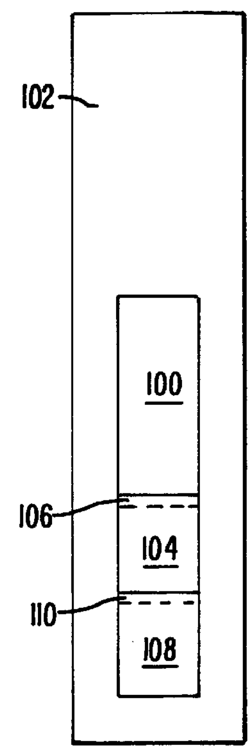
Figure 6D:
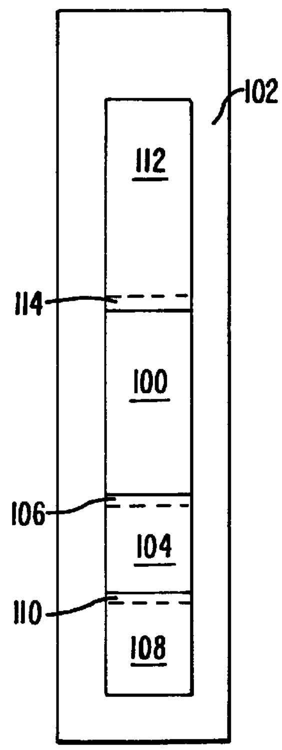

A 20×9 mm strip of the capture zone membrane 100 was affixed centrally on an adhesive transparency strip 102, as shown in FIG. 6A. The transparency strip is a 700×17 mm strip of P 2200 adhesive (3M) with double-sided adhesive tape 444(3M). Label pad 104 was then affixed onto the adhesive strip 102 next to the capture zone pad with a 1 mm overlap 106. Sample receiving pad 108 was then placed next to label pad 104 with 1 mm overlap 110. The device is then provided with an absorbent pad 112 (20×9 mm rectangle of ED No. 939 absorbent) which was affixed to the distal end of the capture zone membrane 100 with a 1 mm overlap 114. The resulting test strip on the transparency backing is then covered with a plastic top, with the length of the strip being centrally within a groove in the bottom surface of the plastic top. Capture lines are exposed in the viewing window, and a sample application hole is immediately above the sample receiving pad. Finally, a bottom of the device, which is a 700×17 mm bottom strip of 1 mm thick opaque white plastic made adhesive with double-sided adhesive tap (3M) was attached to the other side of the transparency strip 102.

Example 2

Preparation of a Pre-dyed Label Complex-Based Device

In a manner analogous to that set forth in Example 1, a second device containing pre-dyed label was prepared. The preparation of the sample receiving pad, the capture zone membrane, and the assembly of the components on backing was identical to that set forth set forth in Example 1. The labelling zone pad contains the same "control" bead, but the Chlamydia specific "test" label was prepared as described below.

Preparation of Anti-Chlamydia-HRP Conjugate

To prepare antibody-enzyme conjugates, horseradish peroxidase (HRP) was dissolved at 10 mg/ml in 0.1 M sodium phosphate (pH 8.0) containing 0.5 mM 2-mercaptoethanol and incubated at 25° C. for 45 min with 2-iminothiolane at a final concentration of 1.23 mg/ml, before being buffer-exchanged on a G25 column into 0.1 M sodium phosphate (pH 7.3).

Maleimide groups were introduced into monoclonal anti-Chlamydia label antibody at 5 mg/ml in 0.1 M sodium phosphate buffer (pH 7.0) by adding n-maleimidobenzoyl-N-hydroxysuccinimide ester (Pierce) at 8 mg/ml in anhydrous DMF to a final concentration of 400 $\mu$g/ml, incubation of the reaction mixture for 45 minutes at 25° C., and buffer exchange on a G25F column into 0.1 M sodium phosphate buffer (pH 7.0).

The maleimide-containing anti-Chlamydia label antibody and SH-derivatized enzyme were allowed to react for 2 hours at 25° C. followed by separation of the enzyme-antibody conjugate on a SEPHACRYL® S300 HR resin (Pharmacia Biotech, Inc.) in 100 mM phosphate buffer, pH 7.0. The fractionation is monitored at 280 mm, and the antibody-enzyme conjugate fraction pooled. Alternatively, unconjugated HRP was separated from antibody-enzyme conjugate using QAE resin. Subsequently, the antibody-enzyme conjugates were buffer-exchanged on a G25 column into 100 mM phosphate buffer pH 7.0.

Preparation of the Pre-Dyed Chlamydia Labeling Complex

Directly before preparation of the dyed label complex, the HRP-anti-Chlamydia conjugate was diluted to 0.3–0.6 mg/ml, and sodium azide and TWEEN®-20 were added to 0.1% and 0.4%, respectively. After 15 min incubation at room temperature, 36.8 $\mu$l of the conjugate was added to 863 $\mu$l reaction mixture preincubated at 15° C. and composed of 4-chloro-1-naphthol at 0.55 mg/ml, hydrogen peroxide at 0.016%, EDTA at 0.08 mM, MBTH at 1 mM, NaCl at 8 mM, gentamycin at 40 μl/ml and 18.6% in 40 mM tris buffer pH 7.5. The accumulation of the red color progressed with the reaction time.

To stop the reaction, 100 μl of methylated BSA at 100 mg/ml was added per reaction at 10, 20 or 30 min, the mixture was further diluted with methylated BSA at 10 mg/ml in 100 mM TRICINE buffer, pH 8.0, supplemented with the blue "control" bead at 0.04%. The mixture was poured onto Sontara spunlace fabric at 39 μl/cm$^2$ and lyophilized as described in Example 1.

Example 3

Conduct of an Chlamydia Assay

Suspensions of the McCoy cells infected with *C. trachomatis* sevovar D/UW$_3$ were diluted with PBS/BSA buffer to different infectivity levels, and 100 μl of the dilutions were spiked on Dacrons® swabs (to 100–1000 IFU/swab). Negative samples were prepared by spiking 100 μl of the buffer itself. The Chlamydia antigen was extracted by 1–5 min incubation with 5 drops (approximately 300 μl) of 0.05–0.3 N NaOH containing 0.05–0.3 M NaCl. The extract was then neutralized with one dropper (approximately 600 μl) of 0.025–0.15 N NaCl containing 10–30 mg/ml of BSA, 0.25–0.4% of the CHAPS detergent and 0.05–0.3% M TRICINE, pH 9.0. The swab was removed after squeezing out soaked-in extract, and the extraction tube was provided with the dropper tip.

The device of Example 1 or of Example 2 was placed flat on a benchtop, and three drops of the extracted liquid sample at approximately 40 μl per drop were applied through sample port 124 to the sample receiving pad 108 (FIGS. 6A–6D). The liquid sample was allowed to flow through the three zones (108, 104, and 100 in order) in nonbibulous lateral flow contact to the absorbent zone 112. A light-blue control band 24 (FIG. 4) appeared at the distal portion of the viewing window 36 in less than a minute when both negative and Chlamydia positive samples were tested. If Chlamydia is present in the sample at least 100 IFU/ml, an additional dark-blue band 22 (FIG. 5) in the analyte capture region was visible in the device of Example 1 or an additional red band appeared in the device of Example 2 within maximum 10 min. At higher levels of the antigen in the sample the test band was more intense and appears sooner. Chlamydia-negative samples produced only the light-blue control band 24.

Example 4

Analytical Sensitivity of the Chlamydia Assay

Eighteen strains of 15 serovars of *C. trachomatis*, TWAR strain of *C. pneumoniae* and three strains of *C. psittaci* were obtained from the ATCC with culture titers subsequently normalized to IFU/ml (number of inclusion forming units per 1ml of undiluted stock). Serial dilutions of the stock in PBS/BSA buffer were prepared and tested in triplicate as 100 μl spiked-on Dacron® swab in the device of the present invention, as described in Example 3. One spiked Dacron® swab was tested in Kodak SureCell™ according to the package insert for the purpose of comparison. The limit of detection was defined as IFU/swab corresponding to the lowest dilution testing positive.

Figure 7A:
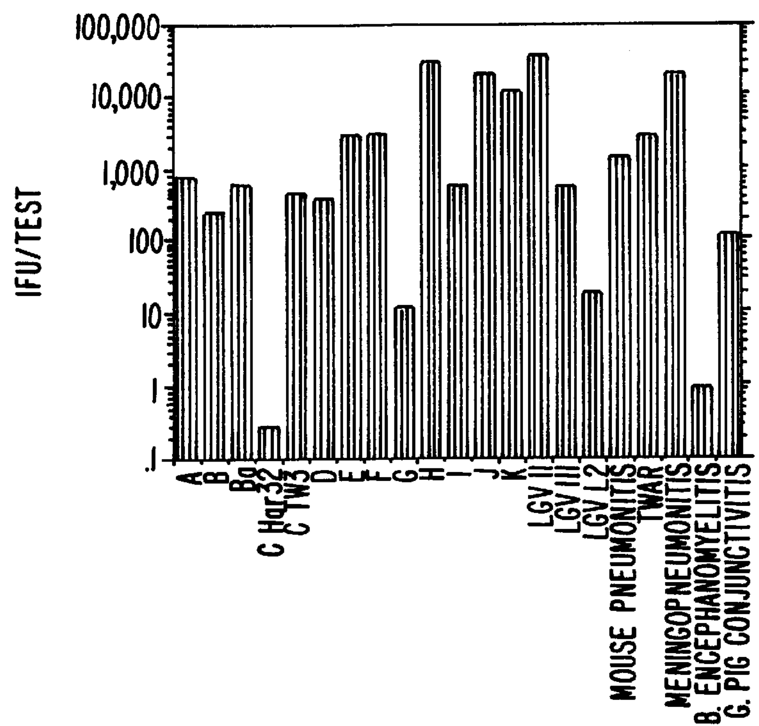
FIGS. 7A and 7B compare the organism sensitivities of a prior art device with those of the device of the present invention.
Figure 7B:
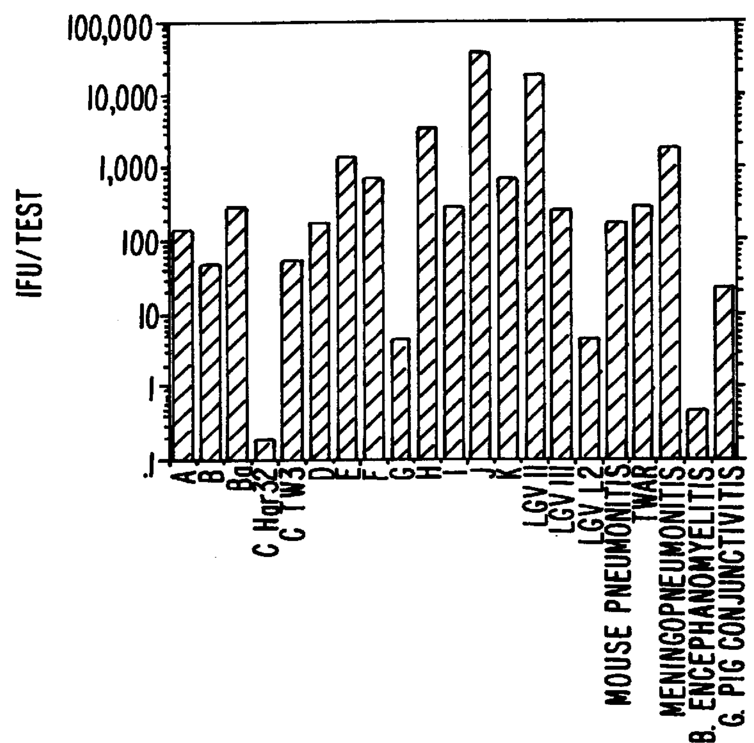

Logarithmic plots of limits of detection of Chlamydia agents by the SureCell™ device and the device of the present invention are presented in FIGS. 7A and 7B, respectfully. Both immunoassays employ genus-specific LPS monoclonal antibodies and thereby they detect all three species of Chlamydia and display similar pattern of distribution of their sensitivity among different Chlamydia agents. Except for Serovar J, the device of the present invention was two- to ten-fold more sensitive than the SureCell™ test. A majority (77%) of the clinically relevant *C. trachomatis* serovars tested positive at low, less than 1,000 IFU/test levels corresponding to 1+/2+ culture. Only serovar J required more than 10,000 IFU (4+ culture) to test positive. This strain-dependent variation in sensitivity can result from different culture adaptability of the strain, its expression of the LPS antigen and the actual amount of the microorganism at different levels of infectivity (IFU).

Example 5

Specificity of the Chlamydia Assay

Microorganism stocks, purchased from ATCC, were propagated in culture broth or on enriched agar. Infectivity (CFU/ml) was determined by plating serial dilutions of viable organisms and colony count. The total concentration of organisms (viable and non-viable), in cells/ml was established by the McFarland method on heat inactivated cultures. Propagated stock cultures were tested in triplicate as 100 μl aliquots spiked onto sterile, Dacron®-tipped swabs as described in Example 3. Additionally, the test result of each test was monitored at 10, 30, 60 minutes and overnight.

Table 1 lists the concentrations of the microorganisms testing negative in the device of the present invention. In addition to infectivity (CFU/ml), the actual concentration of the organisms (Cells/ml) is provided to account for non-viable organisms present in the culture. Only five out of forty-eight stocks (asterisked in Table 1) required dilution to test negative, the remaining organisms tested negative at the highest concentration available, as undiluted stocks. Except for *Bacteroides oralis and Staphylococcus aureus*, the non-reactive concentrations were at least $10^8$ cells/ml, or $10^7$ cells/test. None of the microorganisms tested at the levels indicated showed any sign of cross-reactivity in the assay over a period of 60 min from its completion.

TABLE 1

Concentrations of the microorganisms tested negative at 100 μl per swab.

| No. | ATCC # | ORGANISM | CFU/ml | CELLS/ml |
|---|---|---|---|---|
| 1. | 23055 | *Acientobacter calcoaceticus* | $2.0 \times 10^8$ | $2.5 \times 10^8$ |
| 2. | 15309 | *Acientobacter lwoffii* | $1.0 \times 10^8$ | $1.1 \times 10^9$ |
| 3. | 25285 | *Bacteroides fragilis* | $9.0 \times 10^8$ | $5.6 \times 10^8$ |
| 4. | 25845 | *Bacteroides melaninogenicus* | NA | $5.2 \times 10^9$ |
| 5. | 33269 | *Bacteroides oralis* * | $3.5 \times 10^6$ | $2.7 \times 10^7$ |
| 6. | 18804 | *Candida albicans* | $1.0 \times 10^9$ | $9.0 \times 10^8$ |
| 7. | 2001 | *Candida glabrata* | $2.0 \times 10^8$ | $2.7 \times 10^9$ |
| 8. | 62690 | *Candida guilliermondii* | $1.1 \times 10^9$ | $3.0 \times 10^8$ |
| 9. | 2512 | *Candida kefyr* | $1.0 \times 10^9$ | $5.7 \times 10^8$ |
| 10. | 22019 | *Candida parapsilosis* | $1.0 \times 10^9$ | $2.8 \times 10^8$ |
| 11. | 42678 | *Candida tropicalis* | $1.0 \times 10^9$ | $1.9 \times 10^9$ |
| 12. | 13124 | *Clostridium perfringes* | $1.0 \times 10^8$ | $3.4 \times 10^9$ |
| 13. | 373 | *Corynebacterium xerosis* * | $7.0 \times 10^8$ | $2.7 \times 10^9$ |
| 14. | 19433 | *Enterococcus faecalis* | $1.0 \times 10^9$ | $1.4 \times 10^9$ |
| 15. | 10586 | *Escherichia coli* | $1.0 \times 10^9$ | $1.4 \times 10^9$ |
| 16. | 23263 | *Eubacterium alactolyticum* | $1.0 \times 10^8$ | $7.7 \times 10^8$ |
| 17. | 25559 | *Eubacterium lentum* | $2.3 \times 10^9$ | $4.5 \times 10^9$ |
| 18. | 25586 | *Fusobacteria nucleutum* | $6.0 \times 10^7$ | $4.3 \times 10^9$ |
| 19. | 14018 | *Gardenella vaginalis* | $2.0 \times 10^8$ | NA |
| 20. | 19615 | Group A *beta Streptococus* | $1.0 \times 10^9$ | $1.5 \times 10^9$ |
| 21. | 12386 | Group B *beta Streptococus* | $4.0 \times 10^8$ | $2.0 \times 10^9$ |
| 22. | 19418 | *Haemophilus influenzae* | $7.0 \times 10^9$ | $4.5 \times 10^9$ |
| 23. | 13882 | *Klebsiella pneumoniae* | $1.0 \times 10^9$ | $1.6 \times 10^9$ |
| 24. | 9338 | *Lactobacillus fermentum* | NA | $3.5 \times 10^9$ |
| 25. | 14917 | *Lactobacillus plantarum* | $6.0 \times 10^8$ | $3.4 \times 10^9$ |
| 26. | 17967 | *Moraxella lacunata* | $3.0 \times 10^8$ | $5.4 \times 10^8$ |
| 27. | 23114 | *Mycoplasma hominis* | $1.0 \times 10^8$ | $3.3 \times 10^9$ |
| 28. | 19424 | *Neisseria gonorrhoeae* | $3.0 \times 10^9$ | 1.6 × |
| 29. | 23970 | *Neisseria lactamicus* | $5.0 \times 10^8$ | $4.4 \times 10^8$ |

TABLE 1-continued

Concentrations of the microorganisms tested negative at 100 μl per swab.

| No. | ATCC # | ORGANISM | CFU/ml | CELLS/ml |
|---|---|---|---|---|
| 30. | 13077 | *Neisseria meningitidis* | $1.0 \times 10^8$ | $4.3 \times 10^8$ |
| 31. | 12386 | Non hemolitic Strep B. | $2.9 \times 10^8$ | $5.4 \times 10^9$ |
| 32. | 14963 | *Peptococcus assacharolyticus* | $2.7 \times 10^8$ | $5.1 \times 10^9$ |
| 33. | 9321 | *Peptococcus prevotti* * | $9.0 \times 10^8$ | $1.4 \times 10^9$ |
| 34. | 27337 | *Peptostreptococcus anaerobius* * | $2.1 \times 10^7$ | $5.2 \times 10^9$ |
| 35. | 27340 | *Peptostreptococcus* products | $4.5 \times 10^7$ | $2.6 \times 10^9$ |
| 36. | 14157 | *Propionibacterium propionicum* | $1.2 \times 10^9$ | $4.6 \times 10^9$ |
| 37. | 25933 | *Proteus mirabilis* | $5.0 \times 10^8$ | $2.5 \times 10^9$ |
| 38. | 27973 | *Proteus vulgaris* | $1.0 \times 10^8$ | $3.9 \times 10^8$ |
| 39. | 27853 | *Pseudomonas aeruginosa* | $2.0 \times 10^9$ | $9.0 \times 10^8$ |
| 40. | 9763 | *Sacharomyces cerevisiae* | $4.0 \times 10^8$ | $1.1 \times 10^9$ |
| 41. | 9700 | *Salmonalla minnesota* | $1.1 \times 10^9$ | $3.8 \times 10^9$ |
| 42. | 14028 | *Salmonalla typhimurium* | $3.0.\times 10^9$ | $1.9 \times 10^9$ |
| 43. | 12598 | *Staphylococcus aureus* * | $1.3 \times 10^7$ | $5.6 \times 10^6$ |
| 44. | 35547 | *Staphylococcus epideridis* | $9.0 \times 10^8$ | $9.0 \times 10^8$ |
| 45. | 30001 | *Trichomonas vaginalis* | $2.0 \times 10^7$ | $4.7 \times 10^9$ |
| 46. | 27618 | *Ureaplasma urealyticum* | $1.0 \times 10^8$ | $5.0 \times 10^9$ |
| 47. | 17744 | *Veillonella atypica* | $8.2 \times 10^5$ | $1.6 \times 10^9$ |
| 48. | 10790 | *Veillonella parvula* | $1.6 \times 10^9$ | $1.8 \times 10^9$ |

Example 6

Clinical Performance of the Chlamydia Assay

The study was carried out in three clinical sites representing different patient population characteristics such as clinical presentation, risk factor, history and prevalence of sexually transmitted diseases and age. This information was recorded by the clinic obtaining specimens and used for qualification into asymptomatic and symptomatic patients category. The low risk population under study were 38 patients of Obstetrics/Gynecology Clinic and 320 patients of Family Planning Clinic in Galveston, Tex. High risk population studies were carried out at two different clinical sites: Indiana University Medical Center, Indianapolis, Ind. (126 patients of an STD Clinic) and National University Hospital, Reykjavik, Iceland (240 patients of an STD Clinic).

Three endocervical swab specimens were sequentially obtained from consenting patients after cleansing the exocervix with a cleaning swab/cotton ball. The Chlamydia transport medium containing the first swab was inoculated onto monolayers of McCoy cells and incubated for 48–72 hours following low-speed centrifugation. Methanol-fixed cultures were stained with fluorescein-conjugated anti-Chlamydia antibody and scanned under the fluorescent microscope for Chlamydia inclusions. Positive cultures, quantitated by IFU/ml, were classified as follows:

| Transport Medium IFU/ml | Culture Class |
|---|---|
| <100 | 1+ |
| 100–1,000 | 2+ |
| 1,000–10,000 | 3+ |
| >10,000 | 4+ |

The second and third swabs were used respectively for the assay of the present invention and the SureCell™ testing by the laboratory technician. The McCoy cell culture served as a reference method for both tests performance evaluation. Discrepancies among the test results were resolved by PCR (Amplicor™, Roche Diagnostic Systems PCR) or Cytospin DFA (Syva MicroTrak™ *Chlamydia Trachomatis* Direct Specimen Test).

A total of 724 paired endocervical Dacrons® swabs were evaluated, 73 of them from patients positive by culture (overall prevalence 10.1%). The data for low and high risk population of asymptomatic and symptomatic patients are summarized in Table 2 and for the combined populations on Table 3. As seen in Table 2, the majority of patients (81% in low risk and 59% in high risk population) were asymptomatic. The prevalence of infection among asymptomatic and symptomatic patients in particular clinical site was similar. It was suggested that sensitivity of non-culture tests can be compromised in asymptomatic patients due to marginal quantities of Chlamydia particles present in infected asymptomatic women. In this study, however, the sensitivity of the SureCell™ test was the same in both populations (90%), while the sensitivity of the device of invention was higher in asymptomatic population (94%). Overall performance of the two tests (Table 3) is comparable, with the device of the present invention being significantly more sensitive in the Indiana University site (IU, 85% vs 69%). Specimens of low culture infectivity were detected by both tests with decreased sensitivity (Table 4) and again, the device of the present invention was more effective than SureCell™ in 1+ culture category (81% vs. 75% sensitivity).

TABLE 2

Comparison of the Lateral Flow Test of the present invention (LFT) and the Kodak SureCell ™ Chlamydia Test Kit culture method in different patient populations.

| Site | Risk | n | Prev % | Test | Sens % | Spec % | PPV % | NPV % | Accur % |
|---|---|---|---|---|---|---|---|---|---|
| | | | | ASYMPTOMATIC POPULATION | | | | | |
| TU | Low | 290 | 4.8 | LFT | 88 | 99 | 88 | 99 | 99 |
| | | | | SureCell ™ | 88 | 100 | 100 | 99 | 99 |
| IU | High | 74 | 9.6 | LFT | 100 | 100 | 100 | 100 | 100 |
| | | | | SureCell ™ | 86 | 100 | 100 | 99 | 99 |
| NU | High | 142 | 17.6 | LFT | 96 | 100 | 100 | 99 | 99 |
| | | | | SureCell ™ | 92 | 100 | 100 | 98 | 99 |
| TOTAL | | 509 | 9.1 | LFT | 94 | 99 | 96 | 99 | 99 |
| | | | | Surecell ™ | 90 | 100 | 100 | 98 | 99 |
| | | | | SYMPTOMATIC POPULATION | | | | | |
| TU | Low | 68 | 4.4 | LFT | 100 | 97 | 67 | 100 | 97 |

TABLE 2-continued

Comparison of the Lateral Flow Test of the present invention (LFT) and the Kodak SureCell ™ Chlamydia Test Kit culture method in different patient populations.

| Site | Risk | n | Prev % | Test | Sens % | Spec % | PPV % | NPV % | Accur % |
|---|---|---|---|---|---|---|---|---|---|
| | | | | SureCell ™ | 100 | 98 | 83 | 100 | 99 |
| IU | High | 52 | 11.5 | LFT | 67 | 100 | 100 | 96 | 96 |
| | | | | SureCell ™ | 50 | 100 | 100 | 94 | 94 |
| NU | High | 98 | 18.4 | LFT | 95 | 98 | 90 | 90 | 97 |
| | | | | SureCell ™ | 100 | 100 | 100 | 100 | 100 |
| TOTAL | | 218 | 12.4 | LFT | 90 | 98 | 87 | 98 | 97 |
| | | | | SureCell ™ | 90 | 99 | 96 | 98 | 98 |

TABLE 3

Comparison of the lateral flow test of the present invention (LFT) and the Kodak SureCell ® Chlamydia Test Kit to primary and corrected culture method in low and high risk patient populations (total: asymptomatic and symptomatic).

| Site | Risk | n | Prev % | Test | Sens % | Spec % | PPV % | NPV % | Accur % |
|---|---|---|---|---|---|---|---|---|---|
| | | | | PRIMARY CULTURE | | | | | |
| TU | Low | 358 | 4.7 | LFT | 88 | 98 | 68 | 99 | 98 |
| | | | | SureCell ™ | 88 | 98 | 71 | 99 | 98 |
| IU | High | 126 | 10.3 | LFT | 85 | 100 | 100 | 98 | 98 |
| | | | | SureCell ™ | 69 | 100 | 100 | 97 | 97 |
| NU | High | 240 | 17.9 | LFT | 95 | 98 | 91 | 99 | 98 |
| | | | | SureCell ™ | 95 | 99 | 95 | 99 | 98 |
| TOTAL | | 724 | 10.1 | LFT | 92 | 98 | 86 | 99 | 98 |
| | | | | SureCell ™ | 89 | 99 | 89 | 99 | 98 |
| | | | | CORRECTED CULTURE | | | | | |
| TU | Low | 358 | 4.7 | LFT | 90 | 99 | 82 | 99 | 98 |
| | | | | SureCell | 91 | 99 | 95 | 99 | 99 |
| IU | High | 126 | 10.3 | LFT | 85 | 100 | 100 | 98 | 98 |
| | | | | SureCell | 69 | 100 | 100 | 97 | 97 |
| NU | High | 240 | 17.9 | LFT | 96 | 99 | 96 | 99 | 98 |
| | | | | SureCell | 96 | 100 | 100 | 99 | 99 |
| TOTAL | | 724 | 10.1 | LFT | 92 | 99 | 92 | 99 | 98 |
| | | | | SureCell | 90 | 99 | 99 | 99 | 99 |

TABLE 4

Clinical Sensitivity of LFT Chlamydia Test and SureCell ™ Chlamydia Test Kit related to quantitation of the primary culture. Low and high risk, asymptomatic and symptomatic populations combined.

| Culture | | | LFT | | | SureCell ™ | | |
|---|---|---|---|---|---|---|---|---|
| IFU/ml | Class | n | TP | FN | Sens | TP | FN | Sens |
| >10,000 | 4+ | 5 | 5 | 0 | 100% | 5 | 0 | 100% |
| 1,000–10,000 | 3+[a]) | 29 | 28 | 1 | 97% | 28 | 1 | 97% |
| 100–1,000 | 2+ | 23 | 21 | 2 | 91% | 20 | 3 | 87% |
| <100 | 1+ | 16 | 13 | 3 | 81% | 12 | 4 | 75% |
| TOTAL | | 73 | 67 | 6 | 92% | 65 | 8 | 89% |

[a]Includes 19 Iceland University specimens quantitated as >3,000 IFU/ml

Although the foregoing invention has been described in some detail by way of illustration and example, for purposes of clarity of understanding, it will be obvious that certain changes and modifications may be practiced within the scope of the appended claims.

What is claimed is:

1. A method for determining the presence or amount of Chlamydia in a solubilized sample from a patient, said method comprising:

providing an endocervical swab sample from the patient;

extracting the swab sample by exposing the swab sample to an alkaline solution having a pH of at least 9.0 for a time sufficient to release a chlamydia lipopolysaccharide antigen from the swab sample;

neutralizing the extract by contact with a zwitterionic detergent and blocking protein in a zwitterionic buffer;

applying the neutralized extract to a matrix defining a flow path comprising at least a labelling zone and a capture zone, wherein the labelling zone comprises a labelling complex comprising a visual label bound to an antibody that specifically binds an epitope of the Chlamydia lipopolysaccharide antigen, wherein said labelling complex is not immobilized on said labelling zone, and wherein the capture zone comprises an immobilized antibody that specifically binds an epitope of the Chlamydia lipopolysaccharide antigen; and observing accumulation of the visual label within the capture zone as a result of binding of the Chlamydia lipopolysaccharide antigen to the labelling complex in the labelling zone, flow of the labelling complex-bound Chlamydia lipopolysaccharide antigen to the capture zone, and capture of the labelling complex-bound Chlamydia lipopolysaccharide antigen by the immobilized antibody in the capture zone; and determining the presence or amount of said Chlamydia in the solubilized sample by detecting the presence or amount of the visual label in the capture zone.

2. The method of claim 1, wherein the labelling complex antibody and the immobilized capture zone antibody each specifically bind an epitope on a KDO moiety of the Chlamydia lipopolysaccharide antigen.

3. The method of claim 2, wherein the labelling complex antibody and the immobilized capture zone antibody specifically bind different epitopes on the KDO moiety of the Chlamydia liposaccharide antigen.

4. The method of claim 2, wherein the labelling complex antibody and the immobilized capture zone antibody specifically bind the same epitope on the KDO moiety of the Chlamydia lipopolysaccharide antigen.

5. The method of claim 1, wherein the extracting and neutralizing steps comprise extraction in NaOH followed by neutralization with 3-[(3-cholamidopropyl)-dimethylammonio]-1-propansulfonate (CHAPS) detergent and bovine serum albumin (BSA) as the blocking protein in N-[2-hydroxy-1,1-bis(hydroxymethyl)ethyl] glycine (TRICINE) buffer.

6. A device for determining the presence or amount of Chlamydia in a solubilized sample, said device comprising:

a matrix defining a flow path comprising at least a labelling zone and a capture zone;

said labelling zone comprising a labelling complex, wherein the labelling complex comprises a visual label bound to an antibody that specifically binds an epitope of a Chlamydia lipopolysaccharide antigen, and wherein the labelling zone further comprises a zwitterionic buffer; and said capture zone comprising an immobilized antibody which specifically binds an epitope of the Chlamydia lipopolysaccharide antigen.

7. The device of claim 6, wherein the labelling complex antibody and the immobilized capture zone antibody each specifically bind an epitope on a KDO moiety of the Chlamydia lipopolysaccharide antigen.

8. The device of claim 7, wherein the labelling complex antibody and the immobilized capture zone antibody specifically bind different epitopes on the KDO moiety.

9. The device of claim 7, wherein the labelling complex antibody and the immobilized capture zone antibody specifically bind the same epitope.

10. The device of claim 6, wherein the flow path further comprises a sample receiving zone upstream of the labelling zone and an absorptive zone downstream of the capture zone.

11. The device of claim 6, wherein the matrix comprises at least one zone of a non-bibulous fabric.

12. The device of claim 11, wherein the non-bibulous fabric is spun polyolefm treated with methylated bovine serum albumin.

13. A kit for determining the presence or amount of Chlamydia in a swab sample, said kit comprising:

a device comprising:

a) a matrix defining a flow path comprising at least a labelling zone and a capture zone;

b) said labelling zone comprising a labelling complex, wherein the labelling complex comprises a visual label bound to an antibody that specifically binds an epitope of a Chlamydia lipopolysaccharide antigen; and c) said capture zone comprising an immobilized antibody which specifically binds an epitope of the Chlamydia lipopolysaccharide antigen;

a swab receptacle;

a first reagent container holding an alkaline solution having a pH of at least 9.0 for extracting a swab sample in the receptacle;

a second reagent container holding a solution of a zwitterionic detergent, a zwitterionic buffer, and an albumin for neutralizing the extract in the swab receptacle prior to application to the device; and packaging for holding the device, the swab receptacle, the first reagent container, and the second reagent container.

14. The kit of claim 13, further comprising a written instruction setting forth the following steps:

insert swab into the swab receptacle;

introduce the reagent from the first container to the receptacle and allow incubation to extract Chlamydia lipopolysaccharide antigen from the swab, introduce the reagent from the second container to the receptacle to neutralize the extract;

squeeze liquid contents of the swab back into the receptacle;

apply contents of the receptacle onto the matrix of the device; and determine accumulation of label within the capture zone of the device.

* * * * *

UNITED STATES PATENT AND TRADEMARK OFFICE

CERTIFICATE OF CORRECTION

PATENT NO. : 5,773,234
DATED : June 30, 1998
INVENTOR(S) : Pronovost et al.

It is certified that error appears in the above-identified patent and that said Letters Patent is hereby corrected as shown below:

Column 11,
Line 22, delete "NaCl", and insert therefor -- HCl --.

Signed and Sealed this

Twenty-third Day of April, 2002

Attest:

Attesting Officer

JAMES E. ROGAN
*Director of the United States Patent and Trademark Office*